United States Patent [19]

Woon et al.

[11] 4,296,750
[45] Oct. 27, 1981

[54] REFASTENABLE PRESSURE-SENSITIVE TAPE CLOSURE SYSTEM FOR DISPOSABLE DIAPERS AND METHOD FOR ITS MANUFACTURE

[75] Inventors: Lin-Sun Woon, Appleton; John C. Wilson, Neenah, both of Wis.

[73] Assignee: Kimberly-Clark Corporation, Neenah, Wis.

[21] Appl. No.: 51,048

[22] Filed: Jun. 22, 1979

[51] Int. Cl.³ ............................................. A41B 13/02
[52] U.S. Cl. .................................................. 128/287
[58] Field of Search ........................ 128/287, DIG. 30

[56] References Cited

U.S. PATENT DOCUMENTS

| | | | |
|---|---|---|---|
| 3,520,303 | 7/1970 | Endres | 128/287 |
| 3,951,151 | 4/1976 | Teed | 128/287 |
| 3,952,745 | 4/1976 | Duncan | 128/287 |
| 4,055,182 | 10/1977 | Mack | 128/287 |
| 4,210,144 | 7/1980 | Sarge et al. | 128/287 |

Primary Examiner—C. Fred Rosenbaum
Attorney, Agent, or Firm—Richard C. Ruppin; William D. Herrick

[57] ABSTRACT

In disposable diapers which are equipped with tape closure means and have an impermeable thin film backing, the improvement in which selected areas of the thin film, which areas serve as tape securement zones when the diapers are in use, have uniformly adhered to that side of the film facing the diaper interior a layer of hot melt adhesive to provide a composite structure in the selected areas having a high resistance to tearing when tensile loads are applied. The hot melt adhesive layer has a lower modulus of elasticity than the film and is applied in heat-softened condition to obtain strong, uniform adherence to the film. In a method for applying the adhesive layer, a wide band of adhesive of predetermined thickness is extruded in heat-softened condition into direct contact with selected areas of a moving web of the film. The adhesive is one which has a Ring & Ball softening point lower than the heat distortion temperature of the film and during application will not thermally degrade or distort the film.

9 Claims, 7 Drawing Figures

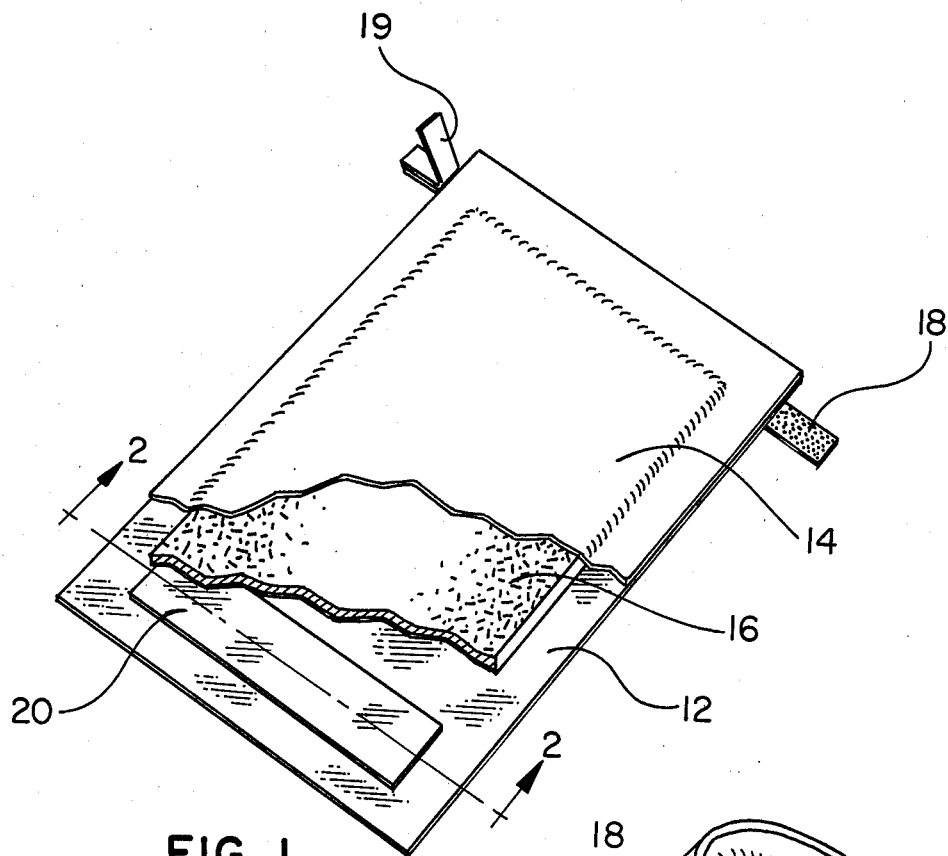
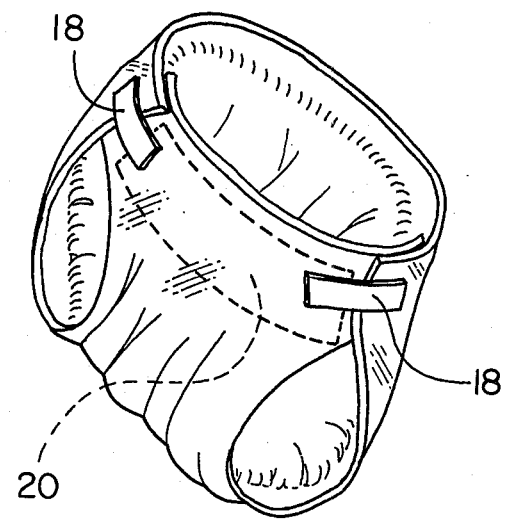

REFASTENABLE PRESSURE-SENSITIVE TAPE CLOSURE SYSTEM FOR DISPOSABLE DIAPERS AND METHOD FOR ITS MANUFACTURE

BACKGROUND OF THE INVENTION

In recent years, the use of disposable diapers in place of reusable cloth diapers has become commonplace, and the market share for disposables is continuing to grow. Disposable diapers commonly comprise a fluid-absorbent pad disposed between a fluid-pervious facing sheet and a thin, flexible, fluid-impervious backing sheet. Most disposable diapers are also usually equipped with a pair of pressure-sensitive tapes which are used to fasten the diaper about the waist of the wearer. When the diapers are manufactured, one end of each tape is permanently secured to a thin film backing sheet near a corner of the diaper while the other free end of the tape is covered by a protective release sheet, which sheet may either be separate or permanently attached to the diaper. When the tape-equipped diaper is made ready for use, the free end of the tape is peeled from the release sheet and secured to the outer thin film side of the diaper after the diaper is positioned on an infant.

The pressure-sensitive adhesive on the tape is formulated to be sufficiently tacky to hold the tape securely in place while in storage, and to insure against disengagement or displacement once the diaper is put on the wearer. Most backing sheets are made of a flexible impermeable film, such as polyethylene, and cost factors dictate that this film be thin and yet provide other needed attributes such as adequate strength, low rattle, high coefficient of friction, etc.

Usually the film is no more than one mil thick. Accordingly, because the film is necessarily thin for economic reasons, if one desires to inspect or adjust the diaper after the tape has been fastened, and in so doing attempts to peel the tape from the film, the usual result is that the thin film will stretch, rupture, and/or tear because of its low tensile load-bearing ability. Further use of the diaper is then impractical, either because the film is torn and weakened, or because adhesive areas of the tape are covered by pieces of film rendering the tape inoperable. When the thin film or tape is damaged by such action, the diaper must be replaced with a new one even though the other components remain substantially undamaged or unsoiled and are otherwise functional.

One suggested solution to the problem is to use tape with a pressure-sensitive adhesive of moderate tack and peel strength which permits peeling the tape off without damage to film or tape and thereby provide refastenability. While the use of a tape with moderate tack permits tape removal with little or no damage to the film or tape components it has been found impractical because the tapes tend to pop off or release spontaneously during use.

Another of the suggested arrangements for solving, or at least ameliorating, this problem is to treat the tape-receiving surface of the film backing sheet itself with a release coating or, alternatively, interposing in the tape-receiving area another tape component having a release-treated surface. Typical patents in this area are U.S. Pat. Nos. 4,020,842 to Richman et al, 4,043,340 to Cepuritis and 4,049,001 to Tritsch. While such release treatment provides easier peel properties, the arrangement also interferes with the initial fastening bond between tape and film, and the security of the bond is compromised. Inadvertent and premature release which might result during use detracts from the desirability of such a system.

Other prior art which has some pertinence to the problem, suggests that the thin film backing be reinforced on its reverse side by laminating to that side a flexible structural material in the area where one end of the tape is secured during manufacture. While emphasis is placed on applying such reinforcement in the area where the tape is first anchored when manufactured, the prior art also broadly suggests reinforcing the area where the free end of the tape is subsequently secured during use.

For example, U.S. Pat. No. 3,867,940 to Mesek et al suggests adhesively laminating to the film a flexible structural material having a higher modulus of elasticity than the film. A high modulus scrim or a polyethylene terephthalate film are specifically suggested as the flexible material for this purpose. However, in such arrangements, it is difficult to obtain a unitary laminate in which the separate layers remain strongly bonded to each other, particularly since a separate bonding agent is used to hold the individual parts together. In addition, complicated process steps are needed to obtain a good laminate. Because of the difficulty in obtaining delamination-resistant bonding, when an attempt is made to peel a strip of high-tack or strongly-adhering tape from the film, the low modulus film tends to stretch and delaminate from the high modulus reinforcement material wherever poor laminar bonding exists causing the film to rupture and/or causing portions of the film to adhere to the pressure-sensitive adhesive. Such situations make refastening impractical. These undesirable results are exacerbated when the reinforcing material has open areas as, for example, when scrim is used.

The present invention overcomes these and other disadvantages by applying to one side of the thin film a layer of compatible hot-melt adhesive, which when applied in hot-melted condition, increases the tear resistance and tensile load bearing ability of the film in the tape securement zones without affecting the ability of the film to securely accept the pressure-sensitive tape.

This above-described uniformly adhered layer of hot-melt adhesive serves to increase the Gurley stiffness of the film-adhesive composite in the selected areas to a stiffness value more closely approaching that of the pressure-sensitive tape itself. The increased stiffness offers a surface which, when the user presses the tape in place, remains firm and keeps the film from deforming in the laminar area. The undeformed surface permits good conformance of tape to the film, and provides a more secure joint between the tape and diaper surface than when a non-stiffened film is the tape-accepting surface, as in the prior art.

In addition, the increased tear resistance of these stiffened areas permits a higher-tack pressure-sensitive tape to be used while assuring that the tape may be peeled from the diaper surface without damaging the film or the pressure-sensitive coating of the tape itself. The improvement thus provides means for reliable refastening, when needed.

In the improved product, the peeling force does not elongate the film beyond its elastic limit during removal and the undeformed surface retains its smooth character which is suitable for reattachment when desired.

Suitable hot-melt adhesives for use in coating the film should have a lower modulus of elasticity than the film, and must have a Ring & Ball softening point lower than the heat distortion temperature of the film so that when applied to the film in hot-melted condition the adhesive will not distort or otherwise thermally degrade the film. The resultant unitary laminate has a structure which is stiffer than uncoated film areas and has a higher elastic limit or yield point then the film alone, and which, as noted above, provides more secure tape attachment. At the same time when the selected areas are subjected to peel stress from a high tack tape the increased tensile load bearing ability in the undercoated areas is such that the film will not delaminate or tear when the tape is pulled away. The film surface is thus left substantially undamaged to permit refastenability when needed.

SUMMARY OF THE INVENTION

This invention is directed to a pressure-sensitive tape closure system for disposable diapers with a thin film backing sheet and in which the film, in the zones where the ends of the tape are secured during use, is modified to increase the Gurley stiffness, elastic limit, tear resistance, and overall tensile load bearing ability of the film in the selected zones. The modification comprises the use of a uniformly adhered layer of hot-melt adhesive with certain specified properties in the selected securement zones. The hot-melt adhesive layer is designed to be of a thickness sufficient to increase the combined tear resistance, elastic limit, stiffness and tensile load-bearing ability of the adhesive and film composite to a degree sufficient to permit an adhered tape to be peeled away without damaging the surface. A suitable hot-melt adhesive is characterized by a number of measurable properties. In the preferred embodiment these properties of the hot-melt adhesive include: (1) a Ring & Ball softening point lower than the heat distortion temperature of the film, in order not to thermally degrade or distort the film surface during application; (2) a lower modulus of elasticity than the film, permitting the composite to flex but not delaminate when peel stress is applied; (3) high Dumbell tensile strength; (4) low elongation; (5) good adhesion to polyolefin film; and (6) good extrudability. The first two properties are the most important, and are considered essential in all embodiments.

The described structure permits a high-tack pressure-sensitive tape, which has been applied to the film-hot-melt adhesive laminate, to be peeled from the film surface in the composite areas without deforming or tearing the film, thus permitting refastenability and secure repositioning of the tape as needed. In practice, the adhesive layer may be applied to an area which extends to the sides and end of the diaper where it can also function as an end and side seal at these peripheral areas of the diaper, if desired.

In the preferred method for applying the hot-melt adhesive to the film, a wide band of heat-softened adhesive of the desired thickness is intermittently extruded into direct contact with selected areas of a moving web of the film at a temperature sufficiently below the heat distoration temperature of the film to permit application without thermally degrading or distorting the film. With such mode of application the opposite side, or working surface, of the film remains substantially unchanged and the initial attachment of tape to that surface will be just as secure as it normally is when attached to unmodified film. More importantly the improved tensile load bearing ability provided by the layer of adhesive permits the tape to be peeled off and refastened without loss of effectiveness.

After application of the heat-softened adhesive, the adhesive-coated film areas may be chilled to set the adhesive more quickly, although chilling is not necessary. Once the hot melt adhesive is set it remains uniformly adhered to the film and provides a substantially unitary composite of the film and the adhesive layer in selected tape securement zones.

Other features, objects and advantages of the invention will become apparent by reference to the accompanying drawings and the following detailed description.

BRIEF DESCRIPTION OF THE DRAWINGS

In the drawings

FIG. 1 is a perspective view, with portions broken away to more clearly show internal structure, of a disposable diaper in open flat configuration illustrating one embodiment of this invention;

FIG. 2 is a sectional view taken along line 2—2 of FIG. 1;

FIG. 3 is a perspective view showing the diaper of FIG. 1 in the approximate configuration assumed when the diaper is in place on the wearer;

DETAILED DESCRIPTION OF PREFERRED EMBODIMENTS

Figure 4:
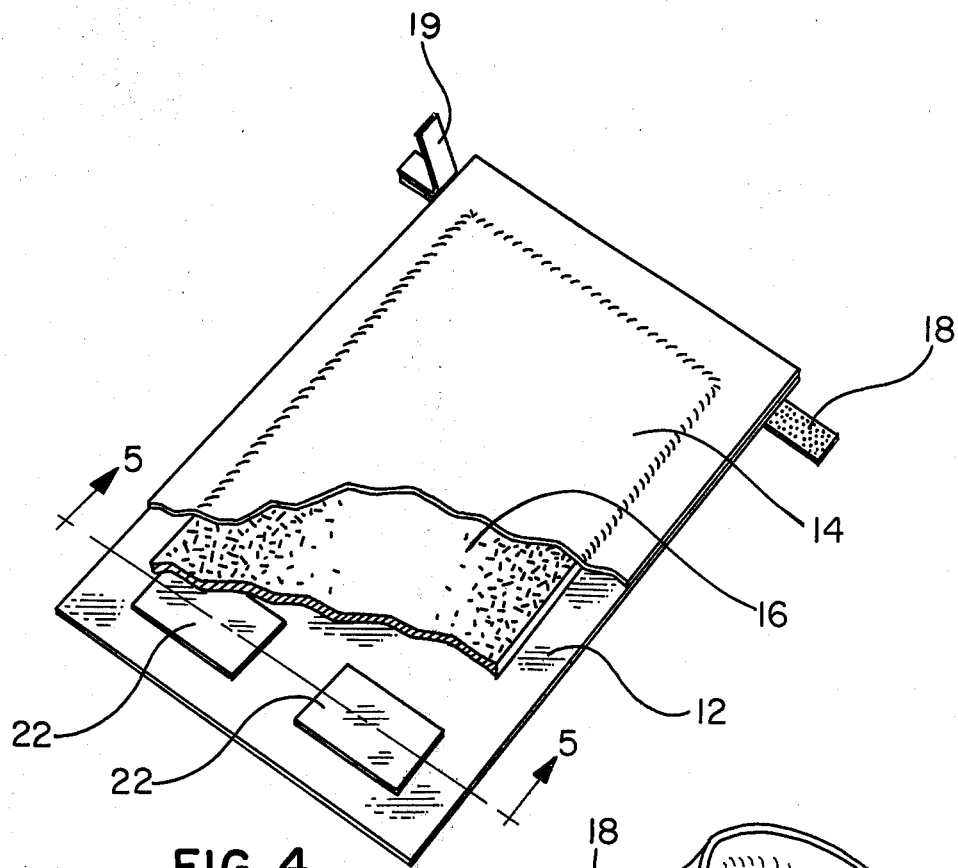
FIG. 4 is a perspective view similar to FIG. 1 of another embodiment of this invention.

In FIG. 1 there is shown a disposable diaper comprised of a fluid-impervious back sheet 12 of thin plastic film such as low density polyethylene; a fluid-pervious body-contacting surface sheet 14 such as a bonded-carded non-woven web of fibers; and a centrally disposed pad 16 of absorbent material such as wood pulp fluff. Disposed at the corners at one end of the diaper are strips of pressure-sensitive tape 18 the free end of which is usually covered by some kind of a removable protective strip 19. At the opposite end of the diaper, spaced inwardly from the ends and sides, there is disposed on the inwardly facing side of film 12 a layer of hot melt adhesive 20 which is uniformly adhered to the film. A sectional view of this latter area is shown in FIG. 2. In a typical example, the coated area is a $2\frac{1}{2}'' \times 6\frac{5}{8}''$ patch spaced about $\frac{3}{4}''$ from the end of the diaper. A larger area may be used, of course, but for economical purposes the smaller the area the better, as long as its area and location meets the primary purpose disclosed herein.

As shown in FIG. 3, the area in which hot-melt adhesive 20 is applied is located in that zone of the diaper where the free ends of tapes 18 are secured when the diaper is in place on the wearer.

Suitable characteristics for composites of adhesive and film incorporating the invention are described in the following examples.

EXAMPLE 1—PRIOR ART

Prior art diapers comprise an absorbent pad disposed between a fluid-pervious liner, and a thin polyethylene film backing sheet of about 1 mil in thickness. Such a film has an average tensile strength in the cross direction of about 1.4 lb./inch of width measured at the yield point of the film which is close to 25% elongation. Attached near opposite corners of the film backing at one end of the diaper are a pair of tape tabs comprised of tape strips having an average peel adhesion, which when attached to a polyethylene-surfaced steel plate, is about 2.5 lb./inch of width. An average peel adhesion value of at least 2.5 lb./inch of width is considered necessary to provide secure attachment in use.

The thin polyethylene film backing had a heat distortion temperature of about 220° F., a modulus of elasticity of about 15,000 psi, an elongation break value in the range of 450% to 600%, and an Elmendorf tear of about 118. The film was too limp to measure for a Gurley stiffness value.

When such a prior art diaper is placed on an infant and the tape secured to the thin-film backing, it provides a reliable securement when first applied, but the tape cannot be peeled from the film without stretching the film beyond its elastic limit and in most cases causing the film to tear. Stress during wear may also tear or distort the film at the taped area. Accordingly, when a user does peel the tape away in order to inspect the diaper to determine if a change is necessary, the tape cannot be reattached because of the damage to the film, and a fresh diaper must be used. If done with extreme care the tape can sometimes be peeled from the film without damage, but this is the exception rather than the rule, and impractical in actual use, because such care is not normally taken by the user.

EXAMPLE 2—FIRST EMBODIMENT

In this Example of a diaper made according to this invention, the structure is the same as in Example 1, except that in the tape attachment area as shown in FIGS. 1 and 2, a 3 mil layer of a hot melt adhesive was applied in heat-softened form to the inside surface of the film backing sheet.

The hot melt adhesive in this Example comprised a Findley formulated amorphous polypropylene #992-334, with a Ring & Ball softening point of between about 198° to 200° F. Because the softening point temperature of this adhesive was less than that of the film, the film did not melt or distort when the hot adhesive was applied.

A 3 mil cast layer of this adhesive, when measured by itself, was found to have a modulus of elasticity of less than 6,000 psi, considerably below that of the thin polyethylene film. The unlaminated cast layer also broke when elongated about 20%, a very low elastic limit, and had a tensile strength of less than 0.5 lb./inch of width.

The film-adhesive composite had a Gurley stiffness of about 35 and an Elmendorf tear of about 428.

When the diaper of this example was placed on an infant, the tape held securely to the undistorted film surface and when it was peeled therefrom, the film-adhesive composite area bowed out slightly as the tape was removed but quickly recovered to its original flat surface and the film did not stretch away from the adhesive, nor did it tear. As a result the tape could be readhered and the closure was substantially as secure as when first applied.

The result was surprising and unexpected since the adhesive layer itself had such a low elastic limit which normally would not be expected to keep the thin film from distorting.

It was also rather surprising that the film-adhesive composite did not distort beyond its elastic limit when the tape was peeled, since a measurement of the composite at yield point or break was about 2.2 lb./inch of width which was slightly below the peel adhesion value of 2.5 lb./inch of width for the tape.

A possible answer might be that the Elmendorf tear of the composite was measured at about 428 which is considerably higher than that of the film alone.

Repeated peel tests of additional diapers with the above characteristics confirmed that the 3 mil thick adhesive layer was enough to provide a refastenable film surface. A series of peeling and refastening tests indicated the film-adhesive composite remained intact more than 80% of the time and thus in the majority of cases permitted refastening because there was no delamination or tearing of the film.

In cases where the tape was inadvertently fastened outside the composite film-adhesive areas, the film did tear in these outside areas. This inadvertent misplacement further confirmed the improved functionality of the composite areas. An ideal product would be one in which all potential fastening areas are made of the composite, eliminating the tape misplacement problem.

EXAMPLE 3—SECOND EMBODIMENT

In general it has been found that a tape with an average peel adhesion of about 2.5 lb./inch of width is sufficient to provide for secure fastening of diapers. However, in some instances it has been found that a higher tack adhesive may be preferred in order to provide positive securement when the user fails to apply sufficient pressure in the initial attachment step. Higher tack tape also works better in instances where the tape or film may be contaminated with talc or baby oil, which often occurs.

When such higher tack adhesives are used therefore it is appropriate to add a thicker layer of hot-melt adhesive to the film. Accordingly, several additional trials were made with tapes having a higher tack adhesive with a peel adhesion value in excess of 2.5 lb./inch of width and a hot-melt layer up to about 5 mil in thickness. In almost every instance, when these were tested, the refastenable characteristic was satisfactory.

As indicated earlier, the hot-melt adhesives suitable for use in this invention should preferably have certain specific properties, i.e., a Ring & Ball softening point less than the heat distortion temperature of the thin polyethylene film, the ability to adhere strongly and uniformly to the film when applied in hot-melted condition, and a lower modulus of elasticity than the film. In addition a cohesive strength as measured by a modified ASTM-638 Dumbell tensile test which provides the necessary tensile strength when adhered to the film is desirable since it provides low elongation properties which will reduce the film stretch when the composite is formed. A range of about 5 to 20 psi and above is desired. Suitable hot-melts in that range are identified later.

Commercial hot-melt adhesives which provide the film with the desired refastenability properties were not easily found from the many candidates tested. Presently preferred is the previously identified Findley #992-334 which is an amorphous polypropylene having a Ring & Ball softening point of about 198° to 200° F.

Adhesives formulated from ethylene vinyl acetate based resins with suitable Ring & Ball softening points also appear to have the necessary properties to obtain refastenability. One adhesive of this latter type which appears to have the necessary characteristics was Fuller #J-4100 which is an ethylene vinyl acetate based hot-melt with a Ring & Ball softening point of about 137° to 140° F.

In general, it can be stated that hot-melt adhesives having a Ring & Ball softening point below 210° F., and preferably above 130° F., may be used in this invention since they will not distort the thin polyethylene film surface when applied in heat-softened condition. The adhesive should also preferably have a sharp softening range, i.e. within about 5° F. and preferably 1° F. for better control.

The adhesive layer should also remain strongly adhered to polyethylene when applied in the temperature range of 210° F. and below. The two adhesives mentioned above meet this latter requirement.

As noted earlier, another measurement which may be used to characterize suitable hot-melt adhesives is high Dumbell tensile, as measured by the modified ASTM D-638 test, of a minimum of 5 psi and preferably 20 psi and above. Dumbell tensiles are also sometimes characterized as cohesive strength. The Dumbell tensile for the Findley #992-334 adhesive was about 8.6 lb./sq. in. and for the Fuller #J-4100 was about 9 lb./sq. in.

While the usual type of thin backing film now used for disposable diapers is low density polyethylene, primarily because of cost, the invention is also applicable to other thin films such as low density polypropylene, blends of polyethylene and polypropylene, or coextruded films of these polyolefins.

Figure 5:
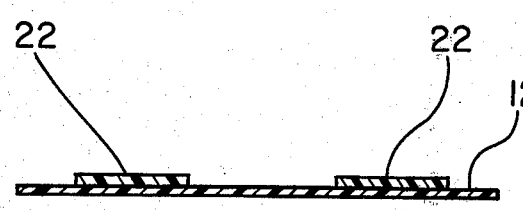
FIG. 5 is a sectional view taken along line 5—5 of FIG. 4.
Figure 6:
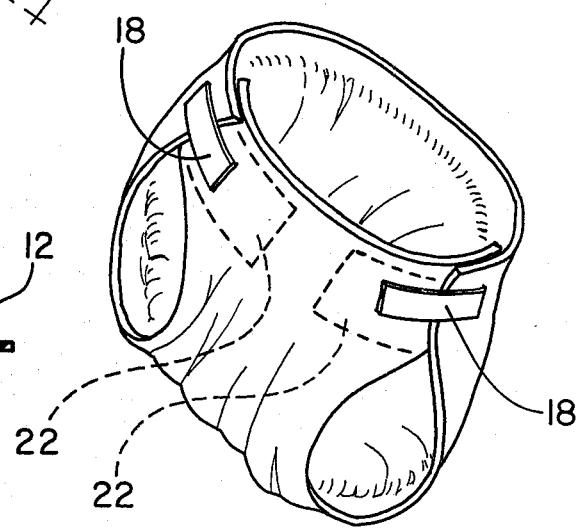
FIG. 6 is a perspective view showing the diaper of FIG. 4 in the approximate configuration the diaper assumes when in place on a wearer.

The securement zone in which the hot-melt layer is applied need not extend across the entire width of the diaper but may be applied in separate patches as shown at 22 in FIGS. 4–6. Such patches are otherwise the same as the single strip shown in FIGS. 1–3.

Figure 7:
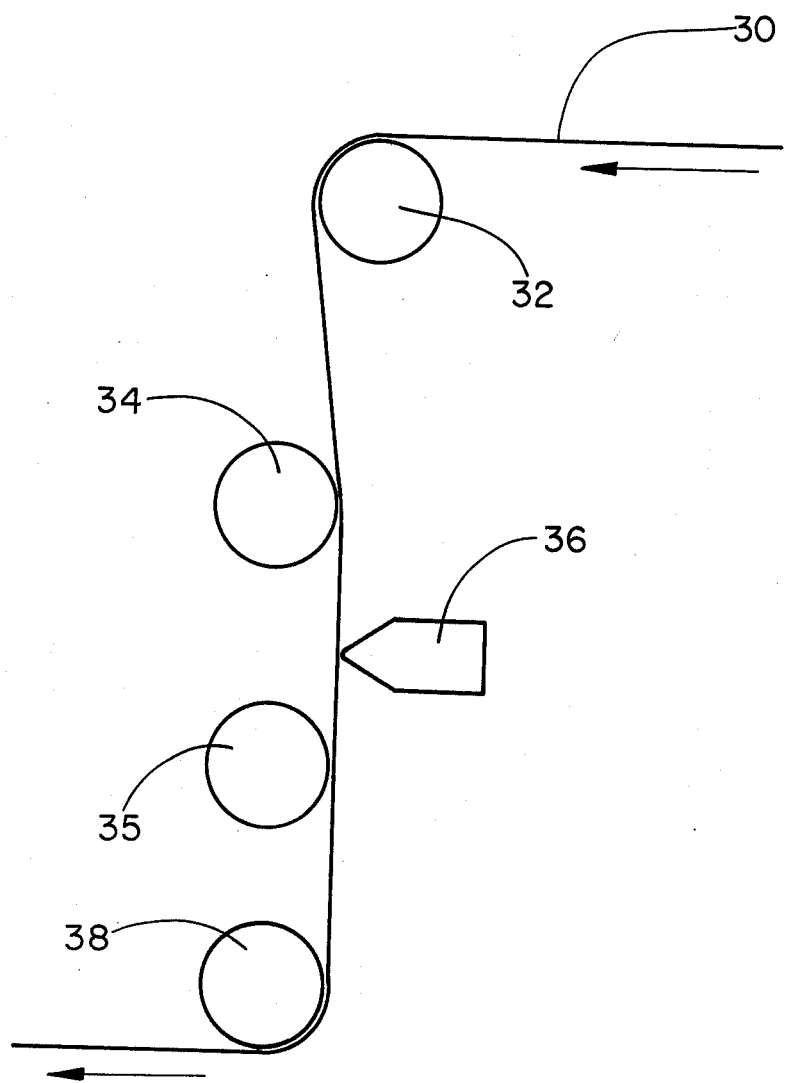
FIG. 7 is a schematic illustration of one method which may be used to apply a layer of hot-melt adhesive to thin film in accordance with the invention.

While the adhesive layer may be applied by hand, a suitable continuous method is preferred. One such method of application is shown in FIG. 7. As shown therein, a continuous web of film 30 is advanced around turning roll 32, over a pair of supporting rolls 34 and 35. The film passes under a hot-melt extruder 36 which contacts the film between supporting rolls 34 and 35 and extrudes the hot-melt intermittently in a layer of the desired thickness. The intermittent extrusion of the hot-melt adhesive is suitably synchronized with the speed of film web 30 and the amount of adhesive being extruded to regulate both the extent of the coating layer and thickness of the layer. After the hot-melt adhesive is applied the coated film is directed around roll 38 and the adhesive allowed to cool and set and to provide firm adherence. Alternatively, the film may be passed around chilled roll to speed the gelling or setting of the adhesive. After application, the film can be sent to storage or proceed on in an in-line operation to fabricate the complete diaper.

While the emphasis is placed on applying the hot-melt layer in the securement zones where the free end of the tape is applied during use, it is understood that the hot-melt layer may also be applied in the corner areas of the diaper to improve the strength characteristics in the areas where the tape is originally applied during manufacture. Still further strength may be obtained by pressing the hot-melt adhesive and diaper components together before the adhesive is set.

The procedures for test values mentioned in the preceding specification are described in the following publications incorporated herein by reference.
1. Tensile load bearing tests—ASTM D-1682-64
2. Elmendorf Tear—ASTM D-1424-63
3. Gurley Stiffness—TAPPI 53 (7): 1316 (1970)
4. Dumbell Tensile—ASTM D-638 as modified
5. Ring & Ball softening point—ASTM E-28

What is claimed is:

1. A pressure-sensitive tape closure system for disposable diapers, said diaper having in combination:
   a fluid permeable facing sheet;
   a backing sheet of a thin polyolefin film attached to the facing sheet along the periphery of the latter;
   an absorbent pad disposed between said facing sheet and said backing sheet;
   a pair of pressure-sensitive tape tab strips having a higher peel adhesion value than the tensile strength and tear resistance of said backing sheet attached to the backing sheet near the diaper corners along a portion of the length of said strips, said unattached portions being designed to engage the exterior of said backing sheet in a predetermined attachment zone; and
   a hot melt adhesive layer having a lower modulus of elasticity and a Ring & Ball softening point lower than the modulus of elasticity and the heat distortion temperature of said backing sheet, respectively, the adhesive layer selectively located in the interior of said backing sheet underneath said attachment zone thereby increasing the stiffness of the film in said zone, said adhesive layer attached only to said backing in said zone.

2. The tape closure system of claim 1 wherein said film is about 1 mil thick and said adhesive layer is about 3 mils thick.

3. The tape closure system of claim 1 wherein said film is less than 1 mil thick and said adhesive layer is about 5 mils thick.

4. The tape closure system of claim 1 wherein said film is about 1 mil thick and said adhesive layer is in the range of 3 to 5 mils thick.

5. The tape closure system of claim 1 wherein said film has a heat distortion temperature above 220° F. and said hot-melt adhesive has a Ring & Ball softening point below 210° F.

6. The tape closure system of claim 5 wherein said Ring & Ball softening point is between 130° F. and 210° F.

7. The tape closure system of claim 1 wherein said hot-melt adhesive is an amorphous polypropylene having a Ring & Ball softening point of about 198° F. to 200° F.

8. The tape closure system of claim 1 wherein said hot-melt adhesive is an ethylene vinyl acetate with a Ring & Ball softening point of about 137° F. to 140° F.

9. The tape closure system of claim 1 wherein the hot-melt adhesive layer is also adhered to the absorbent pad.

* * * * *